United States Patent [19]
Klar et al.

[11] Patent Number: 6,096,732
[45] Date of Patent: Aug. 1, 2000

[54] STEROID ESTERS, PROCESS FOR THEIR PRODUCTION AND THEIR PHARMACEUTICAL USE

[75] Inventors: Ulrich Klar; Arwed Cleve; Wolfgang Schwede; Gunter Neef; Eckhard Ottow; Kristof Chwalisz; Martin Schneider, all of Berlin, Germany

[73] Assignee: Schering AG, Germany

[21] Appl. No.: 08/986,592

[22] Filed: Dec. 8, 1997

[30] Foreign Application Priority Data

Dec. 6, 1996 [DE] Germany .............. 196 52 408

[51] Int. Cl.⁷ .............. A61K 31/56; C07J 53/00
[52] U.S. Cl. .............. 514/179; 552/510; 514/843
[58] Field of Search .............. 514/179, 843; 552/510

[56] References Cited

U.S. PATENT DOCUMENTS

| | | | |
|---|---|---|---|
| 5,095,129 | 3/1992 | Ottow et al. .............. | 552/510 |
| 5,439,913 | 8/1995 | Chwalisz et al. .............. | 514/277 |
| 5,446,178 | 8/1995 | Ottow et al. .............. | 552/510 |
| 5,744,464 | 4/1998 | Elger et al. .............. | 514/179 |

FOREIGN PATENT DOCUMENTS

| | | |
|---|---|---|
| 283428 | 3/1988 | European Pat. Off. . |
| 44 34 448 | 3/1996 | Germany . |
| 44 34 488 | 3/1996 | Germany . |
| 96/19997 | 7/1996 | WIPO . |

*Primary Examiner*—Jose' G. Dees
*Assistant Examiner*—Barbara Badio
*Attorney, Agent, or Firm*—Millen, White, Zelano & Branigan, P.C.

[57] ABSTRACT

Steroid esters of formula I

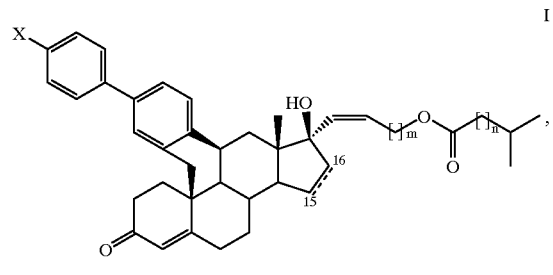

are described, wherein m, n and x are as defined by the specification.

The compounds are distinguished from the basic hydroxy compounds by considerably improved solubility as well by increased biological activity and selectivity.

The compounds are suitable for the production of pharmaceutical agents.

24 Claims, No Drawings

STEROID ESTERS, PROCESS FOR THEIR PRODUCTION AND THEIR PHARMACEUTICAL USE

SUMMARY OF THE INVENTION

The invention relates to steroid esters, process for their production as well as their use as adjuvants for pharmacological studies and as pharmaceutical substances.

The invention relates to steroid esters of formula I

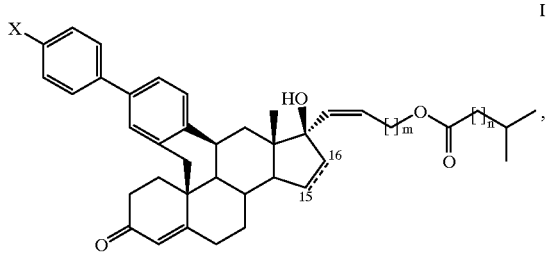

in which
m symbolizes 1 or 2
n symbolizes 0 or 1
x symbolizes F or CN and
the dotted line between carbon atoms 15 and 16 symbolizes the possible presence of a double bond,
excluding the compound (Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estr-4-en-3-one.

The compounds below are especially preferred according to the invention:

(Z)-6'-(4-Cyanophenyl)-9,11α-dihydro-17β-hydroxy-17α-[3-(1-oxo-3-methylbutoxy)-1-propenyl]-4'H-naphtho[3',2',1':10,9,11]estr-4-en-3-one (Z)-6'-(4-cyanophenyl)-9,11α-dihydro-17β-hydroxy-17α-[4-(1-oxo-2-methylpropoxy)-1-butenyl]-4'H-naphtho[3',2',1':10,9,11]estr-4-en-3-one (Z)-6'-(4-cyanophenyl)-9,11α-dihydro-17β-hydroxy-17α-[4-(1-oxo-3-methylbutoxy)-1-butenyl]-4'H-naphtho[3',2',1':10,9,11]estr-4-en-3-one (Z)-9,11α-dihydro-6'-(4-fluorophenyl)-17β-hydroxy-17α-[4-(1-oxo-3-methylbutoxy)-1-butenyl]-4'H-naphtho[3',2',1':10,9,11]estr-4-en-3-one (Z)-6'-(4-cyanophenyl)-9,11α-dihydro-17β-hydroxy-17α-[3-(1-oxo-3-methylbutoxy)-1-propenyl]-4'H-naphtho[3',2',1':10,9,11]estra-4,15-dien-3-one (Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estra-4,15-dien-3-one.

Many steroidal compounds, especially those with an 11-aryl radical, are partially very poorly soluble because of their substitution pattern, so that to preserve therapeutically Ad relevant plasma levels, often superproportionally high single or multiple dosages or expensive formulation techniques must be used.

DE-A 44 34 488 describes that the solubility of such compounds can be significantly improved if a free hydroxyl group is esterified or provided with an amide group at a suitable point in the molecule. The alkanoyloxy group of the ester grouping in the general formula has at least 6 carbon atoms there in the structurally closest cases, i.e., in the case of a 3-keto-4-ene-11β,19-[4-(4-subst.-phenyl)-o-phenylene] steroid with a 17α-alk-1-enyl side chain. In addition, (Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estr-4-en-3-one (reference compound 3) is described as an individual compound.

In addition, 3-keto-4-ene-11β,19-[4-(4-subst.-phenyl)-o-phenylene] steroids with a 17α-alk-1-enyl side chain with a terminal hydroxy group are described in EP-A 0 283 428; the hydroxy group can be esterified with an acyl group with up to 4 carbon atoms. Special esters are not described.

The compounds according to the invention of general formula I thus fall neither within the scope of DE-A 44 34 488 nor are they previously described in EP-A 0 283 428.

It has now been found that the compounds of general formula I, surprisingly enough, differ both with respect to their active strength and their selectivity, i.e., by their entire profile of action, from DE-A 44 34 488.

It has been shown that, surprisingly enough, an empirical correlation exists between the (temperature-dependent) solubility of steroid esters, as they are described in, for example, DE-A 44 34 488 as well as in Examples 1 to 6 of this application, in a mixture of benzyl benzoate/castor oil and their biological activity after oral administration. Solubility that is increased in this solvent system generally results in increased activity of the compounds after oral administration.

The invention also relates to a process for the production of steroid esters of formula I, in which compounds of formula II, which carry a free hydroxyl group and in which m, X and the dotted line between carbon atoms 15 and 16 have the meanings that are indicated in formula I, are esterified with an acid anhydride of formula III or an acid chloride of formula IV, in which n has the value of 0 or 1.

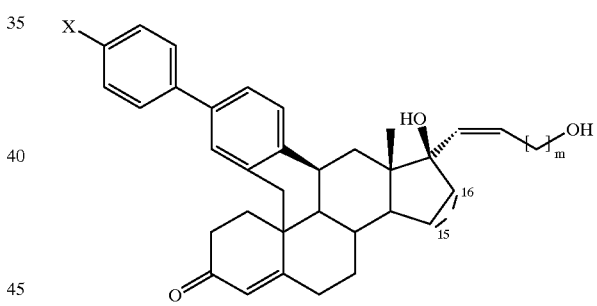

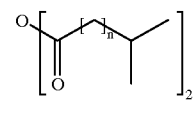

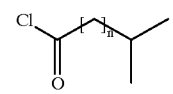

The esterification is done according to the methods that are familiar to one skilled in the art, for example according to the procedure that is described in Example 1.

Solubility Studies of the Esters that are Mentioned in Examples 1 to 6

(1) (Z)-6'-(4-Cyanophenyl)-9,11α-dihydro-17β-hydroxy-17α-[3-(1-oxo-3-methylbutoxy)-1-propenyl]-4'H-naphtho[3',2',1':10,9,11]estr-4-en-3-one (2) (Z)-6'-(4-cyanophenyl)-9,11α-dihydro-17β-hydroxy-17α-[4-(1-oxo-2-methylpropoxy)-1-butenyl]-4'H-naphtho[3',2',1':10,9,11]estr-4-en-3-one (3) (Z)-6'-(4-cyanophenyl)-9,11α-dihydro-17β-hydroxy-17α-[4-(1-oxo-3-methylbutoxy)-1-butenyl]-4'H-naphtho[3',2',1':10,9,11]estr-4-en-3-one (4) (Z)-9,11α-dihydro-6'-(4-fluorophenyl)-17β-hydroxy-17α-[4-(1-oxo-3-methylbutoxy)-1-butenyl]-4'H-naphtho[3',2',1':10,9,11]estr-4-en-3-one (5) (Z)-6'-(4-cyanophenyl)-9,11α-dihydro-17β-hydroxy-17α-[3-(1-oxo-3-methylbutoxy)-1-propenyl]-4'H-naphtho[3',2',1':10,9,11]estra-4,15-dien-3-one (6) (Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estra-4,15-dien-3-one.

In the following table, the solubility of compounds 1 to 6 is depicted in comparison to unesterified reference compound 1 (Z)-6'-(4-cyanophenyl)-9,11α-dihydro-17β-hydroxy-17α-(3-hydroxy-1-propenyl)-4'H-naphtho[3',2',1':10,9,11]estra-4-en-3-one (Example 1 in DE-A 4216003). For solubility, the temperature is indicated in °C., in which 50 mg of substance is dissolved in 1 ml of a 1:4 benzyl benzoate/castor oil mixture.

In all cases, the solubility compared to the unesterified compound is significantly improved.

| Compound | State | Solubility |
| --- | --- | --- |
| Reference Compound 1 | crystalline | >>100 |
| Reference Compound 3 | crystalline | 100 |
| 1 | crystalline | 50 |
| 2 | crystalline | 23 |
| 3 | crystalline | 23 |
| 4 | crystalline | 50 |
| 5 | crystalline | 23 |
| 6 | crystalline | <50 |

Studies on Hydrolytic Stability of the Esters According to the Invention

The hydrolytic stability of the esters under strongly basic conditions can be used to assess whether the compounds have adequate stability under physiological conditions.

In each case, 10 mg of compounds 1, 3 and 4 was dissolved at 23° C. in 10 ml of dioxane and mixed with 1 ml of a 1N aqueous sodium hydroxide solution. In each case, 11 samples were drawn, acidified to pH 6 and the ester:alcohol ratio was determined per HPLC. In the graphic visualization, the portion of ester is depicted in percent as a function of the saponification period in hours.

It is shown that especially compounds 1, 3, and 4 that are studied here, even under strongly basic conditions, have very good stability, which is significantly improved compared to reference compound 3.

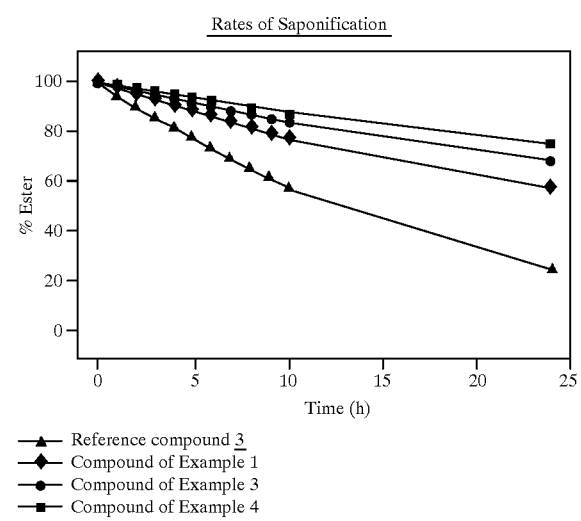

Rates of Saponification

—▲— Reference compound 3
—◆— Compound of Example 1
—●— Compound of Example 3
—■— Compound of Example 4

Abortive Test on Rats as a Measure of Progesterone-Antagonistic Action

Execution of the Test:

Pregnant rats that weigh 190–220 g are used as animal subjects.

The animals are kept in makrolon cages in rooms with controlled lighting (10 hours of darkness, 14 hours of light) at a temperature of 20° C., fed a standard diet (pelletized altromin) and allowed to drink as much tap water as they want.

Galenical Preparation of Substances:

The test substances are suspended in a carrier liquid (85 mg of Myrj in 100 ml of 0.9% w/v of sodium chloride solution), and the daily dose (see Table) is orally administered at a volume of 0.5 ml.

Test Batch:

The rats are paired up in proestrus; the beginning of pregnancy is determined by detection of sperm in the vaginal smear on the day after—this corresponds to day 1 of pregnancy (d1 p.c.). The animals are randomized and assigned at the rate of 4 to 5 animals each to the individual dosage group or control group.

From the 5th to the 7th day of pregnancy, the test substance is administered daily. On the 9th day, vaginal smears are carried out, and the animals are killed with $CO_2$ gas.

Evaluation:

The effect of treatment is studied by inspection of the uterus. The remission of implants, and pathological, hemorrhagic or otherwise abnormal nidation points are classified as abortions.

The results of the rat abortive test of compounds 1 to 6 are listed in the following table. Reference compound 2 is (Z)-6'-(4-cyanophenyl)-9,11α-dihydro-17α-[3-(3,3-dimethyl-1-oxobutoxy)- 1-propenyl]-17β-hydroxy-4'H-naphtho [3',2', 1':10,9,11]estr-4-en-3-one (Example 7 in DE-A 44 34 488), which is distinguished only by an additional methylene group in the alkanoyl group of the ester from compound 1 of this application, as well as reference compound 3, already mentioned.

| Abortion/ Control/ | Reference Compound | | Compound | | | | | |
|---|---|---|---|---|---|---|---|---|
| d p.o. | 2 | 3 | 1 | 2 | 3 | 4 | 5 | 6 |
| 1.0 | 4/4 | nt | nt | nt | nt | nt | nt | nt |
| 0.3 | 2/4 | 5/5 | 5/5 | 4/4 | 4/4 | 4/4 | 4/4 | 4/4 |
| 0.1 | nt | 5/5 | 5/5 | 4/4 | 4/4 | 4/4 | 4/4 | 4/4 |
| 0.03 | nt | nt | 3/5 | 4/4 | 4/4 | 1/4 | 0/4 | 0/4 |
| 0.01 | nt | nt | 1/5 | 0/4 | 0/4 | nt | nt | nt | nt: not tested

Influence of the Tumor Growth in N-Methyl-N-nitrosourea (NMU)—Model in Rats

Biological Basis:

The growth of the NUM-induced breast tumor of rats is largely dependent on estrogens and gestagens and less on prolactin. Estrogen and progesterone antagonists result in inhibiting tumor growth.

Animal Subjects:

Female rats (Sprague-Dawley), 55 (±3) days old; at least 9 animals per group.

Type of Administration:

Test substance: p.o.

Vehicle volume p.o.=0.1 ml/100 g/d (0.9% NaCl/0.085% Myrj-53).

NMU i.v.=50 mg/kg/d; 1.5 ml/200 g (0.9% NaCl/0.085% Myrj-53).

Test Batch:

The animals receive 50 mg/kg of NMU on a one-time basis. Then, the animals are checked once a week by palpation for tumor development. About 6 to 8 weeks after NMU treatment, one or more tumors develop per animal. At a minimum size of 150 mm²/tumor/animal, treatment (6 times per week) begins with the test substance, the determination of body weight and tumor size (with the aid of a sliding gauge; once per week).

The results for compound 1 are graphically depicted in the following figures for various dosages in each case in comparison to the untreated control, an ovariectomy group as well as reference compound 3, (Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estr-4-en-3-one. Both tests quite clearly confirm that compound 1 according to the invention has a tumor-inhibiting action that is superior to that of reference compound 3. This is surprising because of the only slight structural differences.

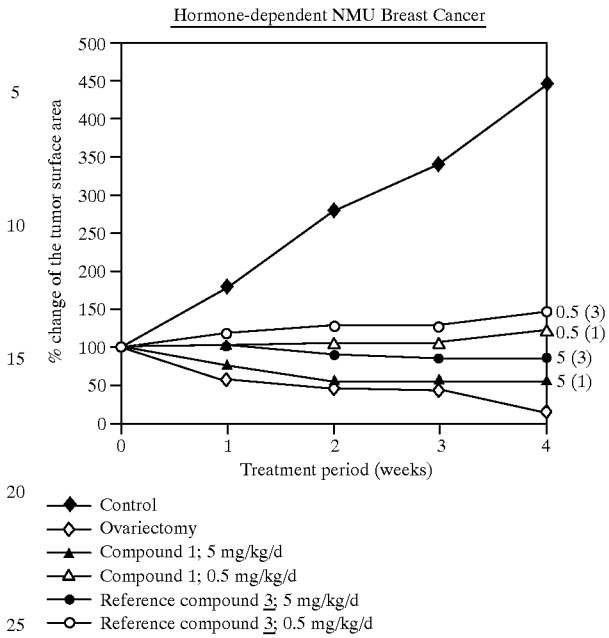

Hormone-dependent NMU Breast Cancer

— ♦ — Control
— ◇ — Ovariectomy
— ▲ — Compound 1; 5 mg/kg/d
— △ — Compound 1; 0.5 mg/kg/d
— ● — Reference compound 3; 5 mg/kg/d
— ○ — Reference compound 3; 0.5 mg/kg/d

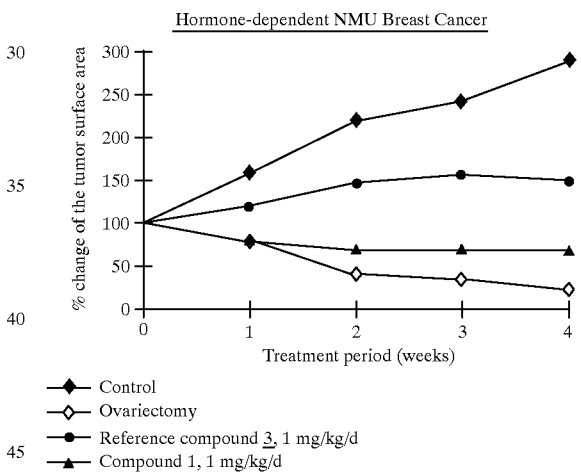

Hormone-dependent NMU Breast Cancer

— ♦ — Control
— ◇ — Ovariectomy
— ● — Reference compound 3, 1 mg/kg/d
— ▲ — Compound 1, 1 mg/kg/d Tumor-Inhibiting Action on the Hormone-Sensitive Human Breast Cancer Cell Line ZR-75.
Biological Basis:
Breast cancer cell line ZR-75 is an estrogen- and progesterone receptor-positive human line, which can be transplanted serially in the thymic aplastic nude mouse. It responds to the standard treatment of breast cancer in clinical practice—tamoxifen—by inhibiting growth. An underline that is used here developed a tamoxifen resistance after a prolonged treatment period.
Animal Subjects:
Female nude/nude mice, 4 weeks old.
Formulation and Administration of Test Substances:
The test substances are dissolved in benzyl benzoate and castor oil (1+4), and the one-time dose is administered at a volume of 0.1 ml s.c. Treatment begins about 7 weeks after implantation (treatment of established tumors). The treatment time is at most 10 weeks.
Test Batch:
The tumor fragments of several donor animals are implanted in the animals s.c. on both sides in the flanks. On the day of implantation and on day 60, all animals are implanted with a tamoxifen-releasing pellet (5 mg).

The mice are randomized 7 weeks after implantation of the tumors, and the treatment is begun and carried out for 8 weeks.

Tumor growth is determined by determination of the tumor surface area using a sliding gauge. The tumor surface area is calculated from the product of the longest diameter of the tumor and the diameter that is perpendicular to said longest diameter. At the end of the test, the animals are killed, the tumors are prepared outside and weighed.
Evaluation:

The inhibition of the course of growth of the tumors is graphically shown in the following figure for the compound of Example 1 in comparison to the untreated control group.

Human, Tamoxifen-Resistant ZR-75 Breast Cancer in Nude Mice

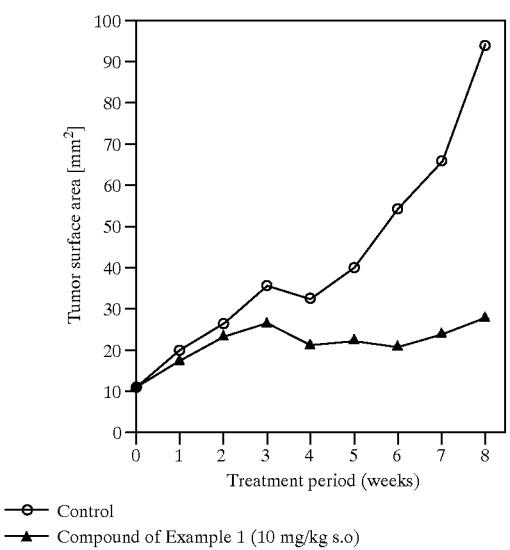

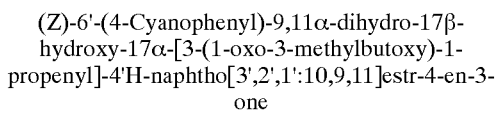

The result confirms that the very good antitumor action that has already been observed in in vitro tests can also be transferred to the in vivo situation.

The new compounds of general formula I are thus valuable pharmaceutical active ingredients. They have a strong affinity to the gestagen receptor and have strong antigestagenic properties. These important biological actions can be used for medicinal purposes.

Active ingredients of this type with pronounced antigestagenic activity are suitable for inducing abortions, since they displace from the receptor the progesterone that is required to maintain pregnancy. They are therefore valuable and advantageous with respect to their use for postcoital birth control.

The compounds of general formula I according to the invention are also suitable for the production of preparations for contraception for the female (e.g., mammal)(WO-A 93/23020).

They can be used, moreover, for hormonal irregularities, for inducing menstruation and for inducing labor. Other types of indications in the field of gynecology are the treatment of symptoms that accompany a dysmenorrhea, e.g., primary and/or secondary dysmenorrhea, as well as endometriosis.

In addition, the compounds according to the invention are highly suitable for the treatment of hormone-dependent carcinomas.

The compounds of general formula I that have an antigestagenic action according to the invention can also be used with compounds that have an antiestrogenic action for the production of pharmaceutical preparations for the treatment of hormone-dependent tumors (EP-A 0 310 542), for inducing labor, for termination of pregnancy as well as for treatment of gynecological disorders (EP-A 0 310 541) and for female contraception (WO 96/19997).

The invention thus also relates to pharmaceutical agents based on the compounds of general formula I that are pharmaceutically compatible, i.e., nontoxic in the doses used, optionally in connection with an antiestrogen, together with commonly used adjuvants and vehicles.

Finally, this invention also relates to the use of the compounds of general formula I, optionally together with an antiestrogen, for the production of pharmaceutical agents.

The compounds according to the invention can be processed into pharmaceutical preparations for enteral, percutaneous, parenteral or topical administration according to methods of galenicals known in the art. They can be administered in the form of tablets, coated tablets, gel capsules, granulates, suppositories, implants, injectable, sterile aqueous or oily solutions, suspensions or emulsions, ointments, creams and gels, or using intravaginal systems (e.g., vaginal rings) or intrauterine systems (pessaries, spirals).

In this connection, the active ingredient or active ingredients can be mixed with the adjuvants that are commonly used in galenicals, such as, e.g., gum arabic, talc, starch, mannitol, methyl cellulose, lactose, surfactants such as Tween or Myrj, magnesium stearate, aqueous or nonaqueous vehicles, paraffin derivatives, wetting agents, dispersing agents, emulsifiers, preservatives and flavoring substances for taste correction (e.g., ethereal oils).

A dosage unit contains about 0.1–100 mg of active ingredient(s). The dosage of the compounds according to the invention in humans is approximately 0.1–1000 mg per day.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 196 52 408.3, filed Dec. 6, 1996 is hereby incorporated by reference.

EXAMPLES

Example 1

(Z)-6'-(4-Cyanophenyl)-9,11α-dihydro-17β-hydroxy-17α-[3-(1-oxo-3-methylbutoxy)-1-propenyl]-4'H-naphtho[3',2',1':10,9,11]estr-4-en-3-one 5.0 g (9.62 mmol) of (Z)-6'-(4-cyanophenyl)-9,11α-dihydro-17β-hydroxy-17α-[3-hydroxy-1-propenyl]-4'H-naphtho[3',2',1':10,9,11]estr-4-en-3-one, whose production is described in detail in DE-A 42 16 004, is dissolved at 23° C. under an atmosphere of dry argon in a mixture of 50 ml of dichloromethane (p.a.) and 30 ml of pyridine (p.a.). Then, it is mixed with 1.99 ml (9.94 mmol) of isovaleric anhydride, 200 mg (1.64 mmol) of 4-dimethylaminopyridine, and it is stirred for 18 hours at 23° C.

It is poured into a saturated sodium bicarbonate solution, stirred for 15 more minutes and extracted several times with dichloromethane. The combined organic extracts are washed with saturated sodium chloride solution and dried on sodium sulfate. The residue that is obtained after filtration and removal of solvent is mixed with toluene, concentrated by evaporation in a vacuum and purified by chromatography on aluminum oxide of activity stage III with a mixture of n-hexane and ethyl acetate.

5.43 g (8.99 mmol, 93.4%) of the title compound is isolated as a crystalline solid, which is dissolved in ethyl acetate at 23° C. and slowly precipitates by adding diisopropyl ether. After filtration and drying, 5.11 g (8.46 mmol, 88.0%) of pure title compound with a melting point of 174–176° C. is obtained.

$^1$H-NMR (CDCl$_3$): δ=0.50 (3H), 0.98 (6H), 1.16 (1H), 1.24–1.47 (4H), 1.65–2.34 (12H), 2.35–2.52 (2H), 2.58 (1H), 2.65 (1H), 3.08 (1H), 3.31 (1H), 3.36 (1H), 4.89 (1H), 5.14 (1H), 5.53 (1H), 5.72 (1H), 5.89 (1H), 7.32 (1H), 7.42 (1H), 7.55 (1H), 7.71 (4H) ppm.

Example 2

(Z)-6'-(4-Cyanophenyl)-9,11α-dihydro-17β-hydroxy-17α-[4-(1-oxo-2-methylpropoxy)-1-butenyl]-4'H-naphtho[3',2',1':10,9,11]estr-4-en-3-one 1.50 g (2.81 mmol) of (Z)-6'-(4-cyanophenyl)-9,11α-dihydro-17β-hydroxy-17α-[4-hydroxy-1-butenyl]-4'H-naphtho[3',2',1':10,9,11]estr-4-en-3-one, which has been produced analogously to the process that is described in DE-A 42 16 004, is reacted analogously to Example 1 with use of isobutyric anhydride, and after working-up and purification, 1.33 g (2.20 mmol, 79%) of the title compound is isolated as a colorless, crystalline solid.

$^1$H-NMR (CDCl$_3$): δ=0.51 (3H), 1.06–1.45 (4H), 1.19 (6H), 1.63–2.13 (9H), 2.28 (1H), 2.42 (2H), 2.53–2.73 (4H), 2.82 (1H), 2.93 (1H), 3.32 (1H), 3.36 (1H), 4.17 (2H), 5.50 (1H), 5.66 (1H), 5.89 (1H), 7.32 (1H), 7.42 (1H), 7.56 (1H), 7.71 (4H) ppm.

Example 3

(Z)-6'-(4-Cyanophenyl)-9,11α-dihydro-17β-hydroxy-17α-[4-(1-oxo-3-methylbutoxy)-1-butenyl]-4'H-naphtho[3',2',1':10,9,11]estr-4-en-3-one 1.5 g (2.81 mmol) of (Z)-6'-(4-cyanophenyl)-9,11α-dihydro-17β-hydroxy-17α-[4-hydroxy-1-butenyl]-4'H-naphtho[3',2',1':10,9,11]estr-4-en-3-one, which has been produced analogously to the process that is described in DE-A 42 16 004, is reacted analogously to Example 1, and after working-up and purification, 1.30 g (2.10 mmol, 75%) of the title compound is isolated as a colorless, crystalline solid.

$^1$H-NMR (CDCl$_3$): δ=0.50 (3H), 0.98 (6H), 1.07–1.46 (4H), 1.56–2.35 (13H), 2.35–2.53 (2H), 2.53–2.73 (3H), 2.81 (1H), 2.90 (1H), 3.31 (1H), 3.35 (1H), 4.17 (2H), 5.50 (1H), 5.67 (1H), 5.90 (1H), 7.32 (1H), 7.42 (1H), 7.57 (1H), 7.71 (4H) ppm.

Example 4

(Z)-9,11α-Dihydro-6'-(4-fluorophenyl)-17β-hydroxy-17α-[4-(1-oxo-3-methylbutoxy)-1-butenyl]-4'H-naphtho[3,2',1':10,9,11]estr-4-en-3-one 465 mg (0.87 mmol) of (Z)-9,11α-dihydro-6'-(4-fluorophenyl)-17β-hydroxy-17α-[4-hydroxy-1-butenyl]-4'H-naphtho[3',2',1':10,9,11]estr-4-en-3-one, which has been produced analogously to the process that is described in DE-A 42 16 004, is reacted analogously to Example 1, and after working-up and purification, 512 mg (0.84 mmol, 96%) of the title compound is isolated as a colorless, crystalline solid.

$^1$H-NMR (CDCl$_3$): δ=0.51 (3H), 0.98 (6H), 1.15 (1H), 1.23–1.45 (3H), 1.63–2.33 (13H), 2.33–2.54 (2H), 2.54–2.73 (3H), 2.80 (1H), 2.91 (1H), 3.31 (1H), 3.35 (1H), 4.17 (2H), 5.50 (1H), 5.67 (1H), 5.88 (1H), 7.12 (2H), 7.26 (1H), 7.37 (1H), 7.50 (1H), 7.75 (2H) ppm.

Example 5

(Z)-6'-(4-Cyanophenyl)-9,11α-dihydro-17β-hydroxy-17α-[3-(1-oxo-3-methylbutoxy)-1-propenyl]-4'H-naphtho[3',2',1':10,9,11]estra-4,15-dien-3-one 50 mg (97 μmol) of (Z)-6'-(4-cyanophenyl)-9,11α-dihydro-17β-hydroxy-17α-[3-hydroxy-1-propenyl]-4'H-naphtho[3',2',1':10,9,11]estra-4,15-dien-3-one, which has been produced analogously to the process that is described in DE-A 42 16 004, is reacted analogously to Example 1, and after working-up and purification, 47 mg (78 μmol, 80%) of the title compound is isolated as a colorless, crystalline solid.

$^1$H-NMR (CDCl$_3$): δ=0.52 (3H), 0.99 (6H), 1.24 (1H), 1.42 (1H), 1.73 (1H), 1.90 (1H), 1.98–2.35 (8H), 2.35–2.53 (2H), 2.53–2.75 (2H), 2.82 (1H), 3.10 (1H), 3.32 (1H), 3.40 (1H), 5.02 (2H), 5.61 (2H), 5.69 (1H), 5.89 (2H), 7.31 (1H), 7.42 (1H), 7.52 (1H), 7.70 (4H) ppm.

Example 6

(Z)-6'-(4-Cyanophenyl)-9,11α-dihydro-17β-hydroxy-17α-[3-(1-oxo-2-methylpropoxy)-1-propenyl]-4'H-naphtho[3',2',1':10,9,11]estra-4,15-dien-3-one 50 mg (97 μmol) of (Z)-6'-(4-cyanophenyl)-9,11α-dihydro-17β-hydroxy-17α-[3-hydroxy-1-propenyl]-4'H-naphtho[3',2',1':10,9,11]estra-4,15-dien-3-one, which has been produced analogously to the process that is described in DE-A 42 16 004, is reacted analogously to Example 1 with use of isobutyric anhydride, and after working-up and purification, 31 mg (53 μmol, 55%) of the title compound is isolated as a colorless, crystalline solid.

$^1$H-NMR (CDCl$_3$): δ=0.53 (3H), 1.20 (6H), 1.26 (1H), 1.43 (1H), 1.73 (1H), 1.91 (1H), 2.00–2.21 (4H), 2.28 (1H), 2.44 (2H), 2.53–2.75 (3H), 2.81 (1H), 3.08 (1H), 3.32 (1H), 3.41 (1H), 5.01 (2H), 5.62 (2H), 5.70 (1H), 5.90 (2H), 7.31 (1H), 7.42 (1H), 7.52 (1H), 7.70 (4H) ppm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A steroid ester of formula I

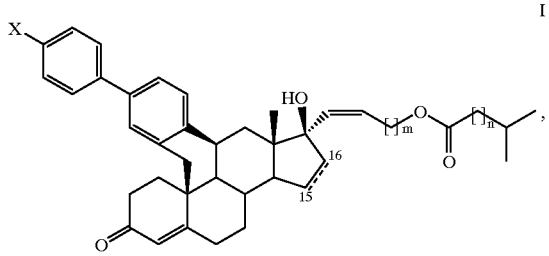

wherein
m is 1 or 2
n is 0 or 1
X is F or CN and
the dotted line between carbon atoms 15 and 16 represents an optional double bond,
with the proviso that the compound of formula I is not (Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estr-4-en-3-one.

2. (Z)-6'-(4-Cyanophenyl)-9,11α-dihydro-17β-hydroxy-17α-[3-(1-oxo-3-methylbutoxy)-1-propenyl]-4'H-naphtho[3',2',1':10,9,11]estr-4-en-3-one,
(Z)-6'-(4-cyanophenyl)-9,11α-dihydro-17β-hydroxy-17α-[4-(1-oxo-2-methylpropoxy)-1-butenyl]-4'H-naphtho[3',2',1':10,9,11]estr-4-en-3-one,
(Z)-6'-(4-cyanophenyl)-9,11α-dihydro-17β-hydroxy-17α-[4-(1-oxo-3-methylbutoxy)-1-butenyl]-4'H-naphtho[3',2',1':10,9,11]estr-4-en-3-one,
(Z)-9,11α-dihydro-6'-(4-fluorophenyl)-17β-hydroxy-17α-[4-(1-oxo-3-methylbutoxy)-1-butenyl]-4'H-naphtho[3',2',1':10,9,11]estr-4-en-3-one,
(Z)-6'-(4-cyanophenyl)-9,11α-dihydro-17β-hydroxy-17α-[3-(1-oxo-3-methylbutoxy)-1-propenyl]-4'H-naphtho[3',2',1':10,9,11]estra-4,15-dien-3-one, or
(Z)-6'-(4-cyanophenyl)-9,11α-dihydro-17β-hydroxy-17α-[3-(1-oxo-2-methylpropoxy)-1-propenyl]-4'H-naphtho[3',2',1':10,9,11]estra-4,15-dien-3-one, each a compound according to claim 1.

3. A compound according to claim 1, in which m has the value of 1.

4. A compound according to claim 1, in which m has the value of 2.

5. A compound according to claim 1, in which n has the value of 1.

6. A compound according to claim 1, in which n has the value of 0.

7. A compound according to claim 1, in which X is a cyano group.

8. A compound according to claim 1, in which X is a fluorine atom.

9. A compound according to claim 1, having a single bond between carbon atoms 15 and 16.

10. A compound according to claim 1, having a double bond between carbon atoms 15 and 16.

11. A process for the production of steroid esters of general formula I according to claim 1, comprising esterifying a compound of formula II, having a free hydroxyl group and in which m, X and the dotted line between carbon atoms 15 and 16 have the meanings that are indicated in formula I, with an acid anhydride of formula III or an acid chloride of formula IV, in which n has the value of 0 or 1

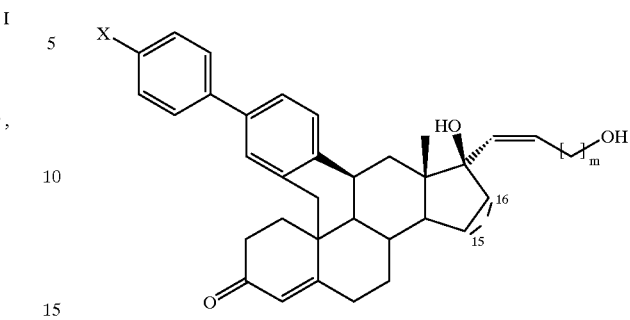

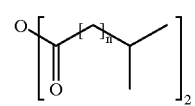

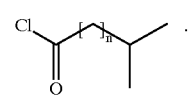

12. A pharmaceutical composition comprising at least one compound of formula I according to claim 1 and a pharmaceutically acceptable carrier. group.

13. A method for achieving an antigestagenic effect in a host in need thereof, comprising administering a compound of claim 1.

14. A method for inducing an abortion or for postcoital birth control in a female mammal in need thereof, comprising administering a compound of claim 1.

15. A method for achieving contraception in a female mammal in need thereof, comprising administering a compound according to claim 1.

16. A method for treating hormonal irregularity or a hormone-dependent carcinoma, comprising administering to a host in need thereof a compound according to claim 1.

17. A method of inducing menstruation or labor in a female mammal in need thereof, comprising administering a compound according to claim 1.

18. A method for treating dysmenorrhea or endometriosis, comprising administering to a female mammal in need thereof a compound according to claim 1.

19. A method for achieving an antigestagenic effect in a host in need thereof, comprising administering a compound of claim 2.

20. A method for inducing an abortion or for postcoital birth control in a female mammal in need thereof, comprising administering a compound of claim 2.

21. A method for achieving contraception in a female mammal in need thereof, comprising administering a compound according to claim 2.

22. A method for treating hormonal irregularity or a hormone-dependent carcinoma, comprising administering to a host in need thereof a compound according to claim 2.

23. A method of inducing menstruation or labor in a female mammal in need thereof, comprising administering a compound according to claim 2.

24. A method for treating dysmenorrhea or endometriosis, comprising administering to a female mammal in need thereof a compound according to claim 2.

* * * * *